United States Patent [19]
Trinnaman

[11] Patent Number: 5,993,879
[45] Date of Patent: *Nov. 30, 1999

[54] METHODS FOR USING 1-METHYLBUTYL AND 1-METHYLHEXYL ESTERS AS FLAVORING AGENTS

[75] Inventor: Laurence Trinnaman, Montvale, N.J.

[73] Assignee: Bush Boake Allen Inc., Montvale, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/953,400

[22] Filed: Oct. 17, 1997

[51] Int. Cl.$^6$ ......................................................... A23L 1/22

[52] U.S. Cl. ............................................ 426/534; 426/650

[58] Field of Search ...................................... 426/534, 650, 426/536, 538, 3, 660

[56] References Cited

U.S. PATENT DOCUMENTS

| | | | |
|---|---|---|---|
| 4,971,813 | 11/1990 | Strobel et al. | 426/51 |
| 5,108,774 | 4/1992 | Mills et al. | 426/599 |
| 5,162,128 | 11/1992 | Mills et al. | 426/599 |

*Primary Examiner*—Leslie Wong
*Attorney, Agent, or Firm*—Richard D. Muccino

[57] ABSTRACT

This invention pertains to a purified flavoring agent represented by the formula:

$$CH_3(CH_2)_nCH(CH_3)OCOR$$

wherein n is 2 or 4 and R is a lower alkyl group having from 1 to 5 carbon atoms. The flavoring agent may be used in a wide variety of ingestible vehicles such as chewing gum compositions, hard and soft confections, dairy products, juice products, and the like. The present invention also pertains to methods for preparing and using the flavoring agents and the ingestible products in which they may be used.

12 Claims, No Drawings

METHODS FOR USING 1-METHYLBUTYL AND 1-METHYLHEXYL ESTERS AS FLAVORING AGENTS

BACKGROUND OF THE INVENTION

1. Field of the Invention

This invention pertains to a purified flavoring agent represented by the formula:

$$CH_3(CH_2)_nCH(CH_3)OCOR$$

wherein n is 2 or 4 and R is a lower alkyl group having from 1 to 5 carbon atoms. The flavoring agent may be used in a wide variety of ingestible vehicles such as chewing gum compositions, hard and soft confections, dairy products, juice products, and the like. The present invention also pertains to methods for preparing and using the flavoring agents and the ingestible products in which they may be used.

2. Description of the Background

The Generessence™ flavor research program conducted by Bush Boake Allen focuses on developing flavors by employing in depth understanding of the volatile organic components present in a wide variety of samples, for example fruits and herbs and coupling this information to flavor preference profiling. A number of sampling and analytical techniques are used including, headspace analysis of the growing sample. The flavors are primarily formulated from synthetic chemicals and contain only components identified in the sample. There is no limit to the concentration of individual components used apart from organoleptic considerations. A problem with developing flavoring agents for fruity materials, such as banana, is that natural fruits do not contain a single flavoring agent, but rather contain a complex mixture of volatile components making identification of characteristic flavors very difficult.

Food Technol. (Chicago) Nov. 23 (1969) 1435; (Issenberg) discloses volatile components identified by capillary column GC-MS analysis in the headspace vapor of banana (Table 4). Z. Naturforsch. B 24 (1969) 781; (Tressel et al.) discloses a gas chromatographic separation of aromatic materials in banana including a table listing 183 flavor compounds, approximately 350 compounds were separated by gas chromatography. Z. Lebensm. Unters. Forsch. 142 (1970) 313; (Tressel et al.) discloses the gas chromatographic identification of 60 esters, 40 alcohols, 28 carbonyl groups, and 4 phenyethers in banana including iso-amyl acetate. Chem. Mikrobiol. Technol. Lebensm. 10 (1986) 120; (Berger et al.) discloses 15 volatile trace components in banana.

While the above disclosures provide some insight into the flavoring components in banana, none of the above disclosures provide satisfactory banana flavoring agents. The present invention provides novel flavoring agents without the disadvantages which are characteristic of previously known products. The flavoring agents may be used in a wide variety of ingestible vehicles. The present invention also provides methods for preparing and using these flavoring agents and the ingestible compositions in which they may be employed.

SUMMARY OF THE INVENTION

The present invention is directed at a purified compound represented by the formula:

$$CH_3(CH_2)_nCH(CH_3)OCOR$$

wherein n is 2 or 4 and R is a lower alkyl group having from 1 to 5 carbon atoms.

The present invention is also directed at an ingestible composition comprising:
(i) an ingestible vehicle; and
(ii) an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The present invention is also directed at a confectionery composition comprising:
(i) a confectionery bulking agent; and
(ii) an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The present invention is also directed at a chewing gum composition comprising:
(i) a gum base;
(ii) a bulking agent; and
(iii) an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The present invention is further directed at a method for flavoring an ingestible composition which comprises admixing an ingestible vehicle with an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The flavoring agent may be used in a wide variety of ingestible vehicles such as chewing gum compositions, hard and soft confections, dairy products, juice products, and the like. The present invention also pertains to methods for preparing and using the flavoring agents and the ingestible products in which they may be used.

DETAILED DESCRIPTION OF THE INVENTION

Applicant has discovered that 1-methylbutyl and 1-methylhexyl esters possess unexpected flavor value and impart a unique note to flavors, especially banana flavors. A relatively large number of components were identified in an analysis of banana flavor, including the 1-methylbutyl and 1-methylhexyl esters. The compounds were tentatively identified by interpretation of their mass spectra and gas chromatographic data and confirmed by synthesis and analysis (IR, NMR and mass spectra). Among the components identified in both the headspace above banana and in the solvent extract of banana were the following esters: 1-methylbutyl acetate, $CH_3(CH_2)_2CH(CH_3)OCOCH_3$, (pentyl-2-yl acetate); 1-methylbutyl butyrate, $CH_3(CH_2)_2CH(CH_3)OCO(CH_2)_2CH_3$, (pentyl-2-yl butyrate); 1-methylhexyl acetate, $CH_3(CH_2)_4CH(CH_3)OCOCH_3$, (heptyl-2-yl acetate); and 1-methylhexyl butyrate, $CH_3(CH_2)_4CH(CH_3)OCO(CH_2)_2CH_3$, (heptyl-2-yl butyrate). The four compounds were present in concentrations between 6.0 and 94.0 parts per thousands of the volatile portion of the samples as calculated from gas chromatographic analysis. Each compound was synthesized for use as an analytical standard and for flavor evaluation. The compounds were believed to be of little flavor use because the compounds were expected to be similar in flavor to the widely available and much cheaper straight chain homologs, amyl and heptyl esters. Instead, these compounds were found to possess unique flavor characteristics and have been successfully incorporated into commercially viable flavors. Although the absolute concentration of these esters in banana was not determined, the esters are present at such low concentrations in banana that they cannot be isolated from the fruit in a commercially viable way. Neither the mixture of esters nor any individual ester was isolated from the fruit. The individual esters, synthesized for analytical confirmation, were submitted for flavor evaluation as individual chemicals and were compared against the common esters, namely iso-amyl acetate) and heptyl acetate.

The following terms are used throughout the specification and are defined as follows unless otherwise indicated.

The terms "ingestible" and "edible", as used herein, refer to all materials and compositions which are used by or which perform a function in the body. These materials and compositions include those which are adsorbed and those which are not absorbed as well as those which are digestible and non-digestible.

The terms "flavor", "flavoring", and "flavorant", as used herein, are used interchangeably whenever an organoleptic compound is referred to which is intended to stimulate the sense of taste and smell.

The term "organoleptic", as used herein, refers to compounds of the invention which stimulate the sense of smell or taste, and are thus perceived as having a characteristic odor and/or flavor. The term "organoleptically acceptable solvent", as used herein, refers to solvents which do not stimulate the sense of smell or taste, and are thus perceived as not having a characteristic odor and/or flavor. The term "organoleptically effective amount", as used herein, means a level or amount of flavoring compound(s) present in a material at which the incorporated compound(s) exhibit(s) a sensory effect.

In accord with the present invention, applicant has discovered flavoring agents in the form of purified compounds represented by the formula: $CH_3(CH_2)_nCH(CH_3)OCOR$; wherein n is 2 or 4 and R is a lower alkyl group having from 1 to 5 carbon atoms. In one embodiment, n is 2, and in another embodiment, n is 4. In one embodiment, R is methyl, and in another embodiment, R is propyl. Preferred purified compounds are 1-methylbutyl acetate, $CH_3(CH_2)_2CH(CH_3)OCOCH_3$, (pentyl-2-yl acetate); 1-methylbutyl butyrate, $CH_3(CH_2)_2CH(CH_3)OCO(CH_2)_2CH_3$, (pentyl-2-yl butyrate); 1-methylhexyl acetate, $CH_3(CH_2)_4CH(CH_3)OCOCH_3$, (heptyl-2-yl acetate); and 1-methylhexyl butyrate, $CH_3(CH_2)_4CH(CH_3)OCO(CH_2)_2CH_3$, (heptyl-2-yl butyrate). More preferred purified compounds are 1-Methylbutyl acetate, 1-methylbutyl butyrate, and 1-methylhexyl butyrate.

The flavoring agents of the present invention may be used in many distinct physical forms well known in the flavoring art to provide an initial dosage of the flavoring agent and/or a further time-release form of the flavoring agent. Without being limited thereto, such physical forms include free forms and encapsulated forms, and mixtures thereof.

The flavoring agents may be used in a wide variety of ingestible vehicles. Nonlimiting examples of suitable ingestible vehicles include chewing gum compositions, hard and soft confections, dairy products, juice products, and the like. The combination of the flavoring agent of the present invention together with an ingestible vehicle and optional ingredients, when desired, provides a flavoring agent that possesses unexpected flavor value and imparts a unique note to flavors, especially banana flavors.

The flavoring agents may further comprise an organoleptically acceptable solvent. The organoleptically acceptable solvent may be any solvent which does not interfere with the organoleptic properties of the flavoring agents of the present invention. In general, the organoleptically acceptable solvent does not stimulate the sense of smell or taste, and is not perceived as having a characteristic odor and/or flavor. Illustrative nonlimiting examples of organoleptically acceptable solvents may be selected from the group consisting of propylene glycol, ethanol, triacetin, glycerol, and vegetable oils. When employed, the organoleptically acceptable solvent will be present in an amount from about 1% to about 99%, preferably from about 5% to about 90%, and more preferably from about 20% to about 80%, by weight.

The amount of the inventive flavoring agent employed in an ingestible composition is an organoleptically effective amount to provide a flavoring agent that exhibits a sensory effect. The exact amount of flavoring agent used may vary depending upon the type of flavoring agent employed, the type of ingestible vehicle employed, and the level of flavor desired. In general, the amount of flavoring agent present is the ordinary dosage required to obtain the desired result. Such dosages are known to the skilled practitioner in the confectionery arts and are not a part of the present invention. In a preferred embodiment, the flavoring agent in the flavoring agent is present in an amount from about 0.001% to about 50%, preferably from about 0.01 % to about 25%, more preferably from about 0.1 % to about 10%, and most preferably from about 0.1% to about 5%, by weight.

A preferred flavoring agent in an ingestible vehicle is a mixture of 1-methylbutyl acetate, present in an amount of from about 2% to about 10%, 1-methylbutyl butyrate, present in an amount of from about 2% to about 10%, and 1-methylhexyl butyrate, present in an amount of from about 0.1 % to about 5%, by weight. Preferably, the preferred flavoring agent is a mixture of 1-methylbutyl acetate, present in an amount of from about 2% to about 8%, 1-methylbutyl butyrate, present in an amount of from about 2% to about 8%, and 1-methylhexyl butyrate, present in an amount of from about 0.1% to about 4%, by weight. More preferably, the preferred flavoring agent is a mixture of 1-methylbutyl acetate, present in an amount of from about 2% to about 6%, 1-methylbutyl butyrate, present in an amount of from about 2% to about 6%, and 1-methylhexyl butyrate, present in an amount of from about 0.1% to about 2%, by weight.

The present invention extends to methods for preparing the flavoring agents. In such a method, the flavoring agent is prepared by admixing one or more flavoring agent in an ingestible vehicle, together with any optional ingredients, to form a uniform mixture. The final compositions are readily prepared using standard methods and apparatus generally known by those skilled in the confectionery arts. The apparatus useful in accordance with the present invention comprises mixing apparatus well known in the confectionery arts, and therefore the selection of the specific apparatus will be apparent to the artisan.

In another embodiment, the present invention is directed at a method for flavoring an ingestible composition which comprises admixing an ingestible vehicle with an organoleptically effective amount of a flavoring agent represented by the formula:

wherein n is 2 or 4 and R is a lower alkyl group having from 1 to 5 carbon atoms.

An important aspect of the present invention includes an improved chewing gum composition incorporating the inventive flavoring agent and a method for preparing the chewing gum composition, including both chewing gum and bubble gum formulations. In general, the improved chewing gum compositions will contain a gum base, a bulking agent, an organoleptically effective amount of a flavoring agent, and various additives such as a flavoring agent.

The chewing gum compositions may be reduced-calorie chewing gums employing high levels of a chewing gum base having an enhanced hydrophilic character. These reduced-calorie chewing gums will comprise a gum base present in an amount from about 50% to about 85%, preferably from about 50% to about 75%, and more preferably from about 60% to about 70%, by weight of the chewing gum composition. When a reduced-calorie product is not desired, the chewing gum composition may contain lower amounts of a chewing gum base.

These chewing gums will comprise a gum base present in an amount up to about 55%, preferably from about 15% to about 40%, and more preferably from about 20% to about 35%, by weight of the chewing gum composition.

As used herein, the term "reduced-calorie composition" means a composition having a caloric value two thirds or less than that of a conventional composition. The term "tight" or "rubbery" chew refers to a chewing gum composition which requires a large amount of muscular chewing effort to masticate or to a composition which provides a gum bolus with high elasticity and bounce and which is difficult to deform.

Gum bases having an enhanced hydrophilic character include polyvinyl acetate gum bases which may also contain a low melting point wax. Such gum bases do not require a high level of bulking agent to plasticize the gum base and render it soft during chewing. These gum bases may be used at higher than normal levels in chewing gum compositions in place of a bulking and/or a bulk sweetening agent to prepare high base-low bulking agent reduced-calorie gums which do not have rubbery or tight chew characteristics. These gum bases possess increased hydrophilic properties over conventional gum bases and appear to increase in size during chewing releasing flavoring and sweetening agents which would normally be entrapped in the gum base while maintaining a soft chew texture. Reduced-calorie chewing gum compositions prepared with such gum bases in high levels are less hygroscopic (have lower moisture-pickup) and are less prone to becoming stale than conventional reduced-calorie gum compositions while having comparable firmness and texture.

The elastomers (rubbers) employed in the gum base of the present invention will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, and the like, and mixtures thereof.

The amount of elastomer employed in the gum base will vary greatly depending upon various factors such as the type of gum base used, the consistency of the gum composition desired and the other components used in the composition to make the final chewing gum product. In general, the elastomer will be present in the gum base in an amount from about 0.5% to about 20%, and preferably from about 2.5% to about 15%, by weight of the gum base.

The polyvinyl acetate polymer employed in the gum base of the present invention is a polyvinyl acetate polymer having a medium molecular weight, specifically, having a mean average molecular weight in the range from about 35,000 to about 55,000. This medium molecular weight polyvinyl acetate polymer will preferably have a viscosity from about 35 seconds to about 55 seconds (ASTM designation D1200-82 using a Ford cup viscometer procedure). The medium molecular weight polyvinyl acetate polymer will be present in the gum base in an amount from about 10% to about 25%, and preferably from about 12% to about 27%, by weight of the gum base.

The medium molecular weight polyvinyl acetate polymer may also be blended with a low molecular weight polyvinyl acetate polymer. The low molecular weight polyvinyl acetate polymer will have a mean average molecular weight in the range from about 12,000 to about 16,000. This low molecular weight polyvinyl acetate polymer will preferably have a viscosity from about 14 seconds to about 16 seconds (ASTM designation D1200-82 using a Ford cup viscometer procedure). The low molecular weight polyvinyl acetate polymer will be present in the gum base in an amount up about 17%, and preferably from about 12% to about 17%, by weight of the gum base.

When a low molecular weight polyvinyl acetate polymer is blended with a medium molecular weight polyvinyl acetate polymer, the polymers will be present in a mole ratio from about 1:0.5 to about 1:1.5, respectively.

The medium molecular weight polyvinyl acetate polymer may also be blended with a high molecular weight polyvinyl acetate polymer. The high molecular weight polyvinyl acetate polymer will have a mean average molecular weight in the range from about 65,000 to about 95,000. The high molecular weight polyvinyl acetate polymer will be present in the gum base in an amount up to about 5 %, by weight of the gum base.

The acetylated monoglycerides in the present invention, like the polyvinyl acetate polymer, serve as plasticizing agents. While the saponification value of the acetylated monoglycerides is not critical, preferable saponification values are 278 to 292, 316 to 331, 370 to 380, and 430 to 470. A particularly preferred acetylated monoglyceride has a saponification value above about 400. Such acetylated monoglycerides generally have an acetylation value (percentage acetylated) above about 90 and a hydroxyl value below about 10 (Food Chemical Codex (FCC) III/P508 and the revision of AOCS).

The use of acetylated monoglycerides in the present gum base is preferred over the use of bitter polyvinyl acetate (PVA) plasticizers, in particular, triacetin. The acetylated monoglycerides will be present in the gum base in an amount from about 4.5% to about 10%, and preferably from about 5% to about 9 %, by weight of the gum base.

The wax in the gum base of the present invention softens the polymeric elastomer mixture and improves the elasticity of the gum base. The waxes employed will have a melting point below about 60° C., and preferably between about 45° C. and about 55° C. A preferred wax is low melting paraffin wax. The wax will be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnauba wax, most petroleum waxes, and the like, and mixtures thereof.

In addition to the components set out above, the gum base includes a variety of traditional ingredients, such as a component selected from the group consisting of elastomer solvents, emulsifiers, plasticizers, fillers, and mixtures thereof. These ingredients are present in the gum base in an amount to bring the total amount of gum base to 100%.

The gum base may contain elastomer solvents to aid in softening the elastomer component. Such elastomer solvents may comprise those elastomer solvents known in the art, for example, terpinene resins such as polymers of alpha-pinene or beta-pinene, methyl, glycerol and pentaerythritol esters of rosins and modified rosins and gums, such as hydrogenated, dimerized and polymerized rosins, and mixtures thereof. Examples of elastomer solvents suitable for use herein include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. A preferred emulsifier is glyceryl monostearate. The emulsifier may be employed in amounts from about 2% to about 15%, and preferably from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20%, and preferably in amounts from about 9% to about 17%, by weight of the gum base.

Preferred plasticizers are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to about 14%, and preferably in amounts from about 5% to about 13.5%, by weight of the gum base.

In another preferred embodiment, the softening agent is anhydrous glycerin, such as the commercially available United States Pharmacopeia (USP) grade. Glycerin is a syrupy liquid with a sweet warm taste and has a sweetness of about 60% of that of cane sugar. Because glycerin is hygroscopic, it is important that the anhydrous glycerin be maintained under anhydrous conditions throughout the preparation of the chewing gum composition.

The gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, and the like, and mixtures thereof. These fillers or adjuvants may be used in the gum base compositions in various amounts. Preferably the amount of filler, when used, will be present in an amount from about 15% to about 40%, and preferably from about 20% to about 30%, by weight of the gum base.

A variety of traditional ingredients may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the gum base.

The manner in which the gum base components are admixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. After blending is complete, the polyvinyl acetate component is admixed into the mixture. The medium molecular weight polyvinyl acetate is preferably admixed prior to addition of the optional low molecular weight polyvinyl acetate to prevent the creation of pockets of polyvinyl acetate within the elastomer mixture. The remaining ingredients, such as the low melting point wax, are then admixed, either in bulk or incrementally, while the gum base mixture is blended again for 1 to 30 minutes.

In one embodiment, the invention pertains to a reduced-calorie chewing gum composition which comprises a gum base present in an amount from about 40% to about 75%, by weight of the chewing gum composition, which comprises (a) an elastomer present in an amount from about 0.5% to about 20%, by weight of the gum base, (b) a medium molecular weight polyvinyl acetate polymer having a molecular weight from about 35,000 to about 55,000 present in an amount from about 10% to about 25%, by weight of the gum base, (c) an acetylated monoglyceride present in an amount from about 4.5% to about 10%, by weight of the gum base, (d) a wax having a melting point below about 60° C. present in an amount from about 6% to about 10%, by weight of the gum base, and (e) a material selected from the group consisting of elastomer solvents, emulsifiers, plasticizers, fillers, and mixtures thereof, present in an amount to bring the total amount of gum base to 100%, by weight of the gum base.

Chewing gum compositions employing a high level of a chewing gum base having an enhanced hydrophilic character are more fully described in U.S. Pat. No. 4,872,884, which disclosure is incorporated herein by reference.

Other gum bases having an enhanced hydrophilic nature and suitable for use in reduced-calorie chewing gum compositions in high levels may also be employed in the present invention. In general, these gum bases may be employed in amounts up to 99%, preferably from about 40% to about 85%, and more preferably from about 40% to about 75%, by weight of the chewing gum composition. Suitable gum bases having an enhanced hydrophilic nature include, for example, those disclosed in U.S. Pat. No. 4,698,223, which disclosure is incorporated herein by reference. The gum base is formulated with the inventive flavoring agent and conventional additives such as a bulking agent to prepare a wide variety of sweetened chewing gum compositions.

The amount of gum base employed in the chewing gum composition will vary depending on such factors as the type of gum base used, the consistency desired, and the other components used to make the final chewing gum product. In general, the gum base having an enhanced hydrophilic character will be present in the chewing gum composition in an amount from about 50% to about 85%, preferably from about 50% to about 75%, and more preferably from about 60% to about 70%, by weight of the chewing gum composition.

In another embodiment, the invention pertains to a chewing gum composition which contains lower amounts of a chewing gum base. In general, the gum base in these chewing gum compositions will be present in an amount up to about 55%, preferably from about 15% to about 40%, and more preferably from about 20% to about 35%, by weight of the chewing gum composition. In this embodiment, the gum base will comprise an elastomer and a variety of traditional ingredients such as an elastomer solvent, waxes, emulsifiers, plasticizers or softeners, bulking agents such as mineral adjuvants which may serve as fillers and textural agents, coloring agents, antioxidants, preservatives, flavoring agents, and the like, and mixtures thereof. Illustrative examples of these gum base components have been set out above.

Once prepared, the gum base may be formulated with the flavoring agent of the present invention and conventional additives to prepare a wide variety of chewing gum compositions.

The chewing gum compositions generally include bulking agents. These bulking agents (carriers, extenders) may be water-soluble and include bulking agents selected from the group consisting of, but not limited to, monosaccharides, disaccharides, polysaccharides, sugar alcohols, and mixtures thereof; isomalt (a mixture of alpha-D-glucopyranosyl-1,6-mannitol and alpha-D-glucopyranosyl-1,6-sorbitol manufactured under the tradename Palatinit by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate, celluloses and the like, and mixtures thereof. Bulking agents may be used in amounts up to about 60%, and preferably in amounts from about 25% to about 60%, by weight of the chewing gum composition.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof. When the chewing gum composition is a sugar gum, mixtures of sucrose and corn syrup solids are the preferred sugar bulking agents.

Suitable sugar alcohol bulking agents include sorbitol, xylitol, mannitol, galactitol, maltitol, and mixtures thereof. Mixtures of sorbitol and mannitol are the preferred sugar alcohol bulking agents.

Maltitol is a sweet, non-caloric, water-soluble sugar alcohol useful as a bulking agent in the preparation of non-caloric beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

The chewing gum compositions may also include a high intensity sweetening agent (sweeteners). High intensity sweetening agents have a sweetness intensity substantially greater than that of sucrose. Suitable high intensity sweetening agents include water-soluble natural sweetening agents such as dihydrochalcones, monellin, Stevia Rebaudiana (steviosides), glycyrrhizin, and mixtures thereof. Suitable water-soluble artificial sweetening agents include saccharin and its soluble salts, i.e., sodium and calcium saccharin salts, cyclamate and its salts, 3,4-dihydro-6-methyl-1,2,3-oxathiazine-4-one-2,2-dioxide (Acesulfame) and the sodium, ammonium, and calcium salts thereof, and especially the potassium salt of 3,4-dihydro-6-methyl-1,2, 3-oxathiazine-4-one-2,2-dioxide (Acesulfame-K).

Suitable dipeptide based sweetening agents include L-aspartic acid derived sweetening agents such as L-aspartyl-L-phenylalanine methyl ester (Aspartame), compounds described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine, and L-aspartyl-L-(1-cyclohexen)alanine.

Other suitable water-soluble sweetening agents include those derived from naturally occurring water-soluble sweetening agents such as chlorinated derivatives of sucrose, e.g., chlorodeoxysugar derivatives such as derivatives of chlorodeoxysucrose and chlorodeoxy-galactosucrose. Examples of chlorodeoxysucrose and chlorodeoxygalactosucrose derivatives include but are not limited to 1-chloro-1'-deoxysucrose; 4-chloro-4-deoxy-alpha-D-galacto-pyranosyl-alpha-D-fructofuranoside, or 4-chloro-4-deoxygalactosucrose; 4-chloro-4-deoxy-alpha-D-galacto-pyranosyl-1-chloro-1-deoxy-beta-D-fructo-furanoside, or 4,1'-dichloro-4,1'-dideoxygalactosucrose; 1',6'-dichloro-1', 6'-dideoxysucrose; 4-chloro-4-deoxy-alpha-D-galacto-pyranosyl-1,6-dichloro-1,6-dideoxy-beta-D-fructo-furanoside, or 4,1',6'-trichloro-4,1',6'-trideoxygalacto-sucrose; 4,6-dichloro-4,6-dideoxy-alpha-D-galacto-pyranosyl-6-chloro-6-deoxy-beta-D-fructo-furanoside, or 4,6,6'-trichloro-4,6,6 '-trideoxygalacto-sucrose; 6,1',6'-trichloro-6,1',6'-trideoxysucrose; 4,6-dichloro-4,6-dideoxy-alpha-D-galacto-pyranosyl-1,6-dichloro-1,6-di-deoxy-beta-D-fructofuranoside, or 4,6,1',6'-tetrachloro-4,6,1',6'-tetradeoxygalacto-sucrose; and 4,6,1',6'-tetrachloro-4,6,1', 6'-tetradeoxy-sucrose. In a preferred embodiment, the chlorodeoxysugar derivative is 4,1',6'-trichloro-4,1',6'-trideoxygalacto-sucrose, or 4-chloro-4-deoxy-alpha-D-galactopyranosyl-1,6-dichloro-1,6-dideoxy-beta-D-fructofuranoside, which is commercially available under the tradename Sucralose from McNeil Specialty Products Company, Skillman, New Jersey.

Other suitable high intensity sweetening agents include protein based sweetening agents such as talin (thaumaoccous danielli, Thaumatin I and II).

The amount of the high intensity sweetening agent employed in the chewing gum composition is an effective amount to sweeten the chewing gum. In general, the amount of high intensity sweetening agent normally present in a chewing gum composition will be from about 0.001% to about 1%, preferably from about 0.01% to about 1%, and more preferably from about 0.05% to about 0.5%, by weight of the chewing gum composition.

The gum composition may include effective amounts of conventional additives selected from the group consisting of plasticizers, softeners, emulsifiers, waxes, fillers, mineral adjuvants, flavoring agents (flavors, flavorings), coloring agents (colorants, colorings), antioxidants, acidulants, thickening agents, and the like, and mixtures thereof. These ingredients are present in the chewing gum composition in an amount to bring the total amount of chewing gum composition to 100%. Some of these additives may serve more than one purpose. For example, in sugarless gum compositions, a sweetening agent, such as sorbitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickening agents, used alone or in combination with other softeners, such as methyl cellulose, alginates, carrageenan, xanthan gum, gelatin, carob, tragacanth, and locust bean, acidulants such as malic acid, adipic acid, citric acid, tartaric acid, fumaric acid, and mixtures thereof, and fillers, such as those discussed above under the category of mineral adjuvants.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include vanilla, spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are natural and synthetic fruit flavors such as citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63–258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (citrus fruits such as orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well known and do not constitute a part of this invention.

The flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof.

Encapsulated delivery systems for flavoring agents or sweetening agents comprise a hydrophobic matrix of fat or wax surrounding a sweetening agent or flavoring agent core. The fats may be selected from any number of conventional materials such as fatty acids, glycerides or polyglycerol esters, sorbitol esters, and mixtures thereof. Examples of fatty acids include hydrogenated and partially hydrogenated vegetable oils such as palm oil, palm kernel oil, peanut oil, rapeseed oil, rice bran oil, soybean oil, cottonseed oil, sunflower oil, safflower oil, and mixtures thereof. Glycerides which are useful include monoglycerides, diglycerides, and triglycerides.

Waxes useful may be chosen from the group consisting of natural and synthetic waxes, and mixtures thereof. Nonlimiting examples include paraffin wax, petrolatum, carbowax, microcrystalline wax, beeswax, carnauba wax, candellila wax, lanolin, bayberry wax, sugarcane wax, spermaceti wax, rice bran wax, and mixtures thereof.

The fats and waxes may be use individually or in combination in amounts varying from about 10 to about 70%, and preferably in amounts from about 40 to about 58%, by weight of the encapsulated system. When used in combination, the fat and wax are preferably present in a ratio from about 70:10 to 85:15, respectively.

Typical encapsulated flavoring agent or sweetening agent delivery systems are disclosed in U.S. Pat. Nos. 4,597,970 and 4,722,845, which disclosures are incorporated herein by reference.

The amount of flavoring agent employed herein is normally a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5%, and preferably from about 0.1 % to about 2%, and more preferably, from about 0.8% to about 1.8%, by weight of the chewing gum composition.

The coloring agents useful in the present invention are used in amounts effective to produce the desired color. These coloring agents include pigments which may be incorporated in amounts up to about 6%, by weight of the gum composition. A preferred pigment, titanium dioxide, may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5'-indigotindisulfonic acid. Similarly, the dye known as F.D.& C. Green No. 1 comprises a triphenylmethane dye and is the disodium salt of 4-[4-(N-ethyl-p-sulfoniumbenzylamino) diphenylmethylene]-[1-(N-ethyl-N-p-sulfoniumbenzyl)-delta-2,5-cyclohexadienimine]. A full recitation of all F.D.& C. colorants and their corresponding chemical structures may be found in the Kirk-Othmer Encyclopedia of Chemical Technology, 3rd Edition, in volume 5 at pages 857–884, which text is incorporated herein by reference.

Suitable oils and fats usable in gum compositions include partially hydrogenated vegetable or animal fats, such as coconut oil, palm kernel oil, beef tallow, lard, and the like. These ingredients when used are generally present in amounts up to about 7%, and preferably up to about 3.5%, by weight of the gum composition.

In accordance with this invention, organoleptically effective amounts of the flavoring agent of the present invention may be admixed into the chewing gum composition. The exact amount of flavoring agent employed is normally a matter of preference subject to such factors as the particular type of gum composition being prepared, the type of bulking agent employed, the type of flavor employed, and the intensity of breath freshening perception desired. Thus, the amount of flavoring agent may be varied in order to obtain the result desired in the final product and such variations are within the capabilities of those skilled in the art without the need for undue experimentation. In general, the amount of flavoring agent normally present in a chewing gum composition will be from about 0.001% to about 20%, preferably from about 0.01% to about 15%, more preferably from about 0.1% to about 10%, and most preferably from about 0.1% to about 5%, by weight of the chewing gum composition.

In a preferred embodiment, the present invention is directed to a chewing gum composition comprising:

(i) a gum base;

(ii) a bulking agent; and (iii) an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The present invention also includes a method for preparing the improved chewing gum compositions, including both chewing gum and bubble gum formulations. The chewing gum compositions may be prepared using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

In such a method, a chewing gum composition is made by admixing the gum base with the flavoring agent and the other ingredients of the final desired chewing gum composition. Other ingredients will usually be incorporated into the composition as dictated by the nature of the desired composition as well known by those having ordinary skill in the art. The ultimate chewing gum compositions are readily prepared using methods generally known in the food technology and chewing gum arts.

For example, the gum base is heated to a temperature sufficiently high to soften the base without adversely effecting the physical and chemical make up of the base. The optimal temperatures utilized may vary depending upon the composition of the gum base used, but such temperatures are readily determined by those skilled in the art without undue experimentation.

The gum base is conventionally melted at temperatures that range from about 60° C. to about 120° C. for a period of time sufficient to render the base molten. For example, the gum base may be heated under these conditions for a period of about thirty minutes just prior to being admixed incrementally with the remaining ingredients of the gum composition such as the inventive flavoring agent, plasticizer, the softener, the bulking agent, and/or fillers, coloring agents and flavoring agents to plasticize the blend as well as to modulate the hardness, viscoelasticity and formability of the base. Mixing is continued until a uniform mixture of gum composition is obtained. Thereafter the gum composition mixture may be formed into desirable chewing gum shapes.

In a preferred embodiment, the invention is directed at a method for preparing a chewing gum composition which comprises the steps of:

(1) providing the following ingredients:
  (i) a gum base;
  (ii) a bulking agent; and
  (iii) an organoleptically effective amount of a flavoring agent;

(2) melting the gum base;

(3) admixing the bulking agent and the flavoring agent with the melted gum base; and (4) forming the mixture from step (C) into suitable shapes.

The flavoring agent is prepared according to the method of the present invention.

Another important aspect of the present invention includes a confectionery composition incorporating the inventive flavoring agent and a method for preparing the confectionery compositions. The preparation of confectionery formulations is historically well known and has changed little through the years. Confectionery items have been classified as either "hard" confectionery or "soft" confectionery. The flavoring agents of the present invention can be incorporated into the confections by admixing the inventive composition into the conventional hard and soft confections.

Hard confectionery may be processed and formulated by conventional means. In general, a hard confectionery has a base composed of a mixture of sugar and other carbohydrate bulking agents kept in an amorphous or glassy condition. The hard confectionery may also be sugarless. This form is considered a solid syrup of sugars generally having from about 0.5% to about 1.5% moisture. Such materials normally contain up to about 92% sugar, up to about 55% corn syrup and from about 0.1% to about 5% water, by weight of the final composition. The syrup component is generally prepared from sucrose and corn syrups, but may include other materials. Further ingredients such as flavorings, sweetening agents, acidulants, colorants and so forth may also be added.

Such confectionery may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavoring agent, colorants and the like.

A high-speed atmospheric cooker uses a heat-exchanger surface which involves spreading a film of candy on a heat exchange surface, the candy is heated to 165° C. to 170° C. in a few seconds. The candy is then rapidly cooled to 100° C. to 120° C. and worked as a plastic-like mass enabling incorporation of the additives, such as flavoring agent, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavoring agent, colorants, and other additives are admixed in the mass by routine mechanical mixing operations.

The optimum mixing required to uniformly mix the flavoring agent, colorants and other additives during conventional manufacturing of hard confectionery is determined by the time needed to obtain a uniform distribution of the materials. Normally, mixing times of from 2 to 10 minutes have been found to be acceptable.

Once the candy mass has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms: Tablets, Volume 1 (1989), Marcel Dekker, Inc., New York, N.Y. at pages 419 to 582, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particular materials and are formed into structures under pressure. These confections generally contain sugars in amounts up to about 95%, by weight of the composition, and typical tablet excipients such as binders and lubricants as well as flavoring agent, colorants and so forth. These confections may also be sugarless.

Similar to hard confectionery, soft confectionery may be utilized in this invention. The preparation of soft confections, such as nougat, involves conventional methods, such as the combination of two primary components, namely (1) a high boiling syrup such as a corn syrup, or the like, and (2) a relatively light textured frappe, generally prepared from egg albumin, gum arabic, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. Soft confectioneries may also be prepared sugarless. A general discussion of the composition and preparation of nougat confections may be found in B. W. Minifie, Chocolate, Cocoa and Confectionery: Science and Technology, 2nd edition, AVI Publishing Co., Inc., Westport, Conn. (1983), at pages 576–580, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor may be added. The mixture is further mixed for an additional period until it is ready to be removed and formed into suitable confectionery shapes.

In accordance with this invention, organoleptically effective amounts of the flavoring agents of the present invention may be admixed into the hard and soft confections. The exact amount of flavoring agent employed is normally a matter of preference subject to such factors as the particular type of confection being prepared, the type of bulking agent or carrier employed, the type of flavor employed and the intensity of breath freshening perception desired. Thus, the amount of flavoring agent may be varied in order to obtain the result desired in the final product and such variations are within the capabilities of those skilled in the art without the need for undue experimentation. In general, the amount of flavoring agent normally present in a hard or soft confection will be from about 0.001% to about 20%, preferably from about 0.01% to about 15%, more preferably from about 0.1% to about 10%, and most preferably from about 0.1% to about 5%, by weight of the confection.

In a preferred embodiment, the present invention is directed to a confectionery composition comprising:

(i) a confectionery bulking agent; and (ii) an organoleptically effective amount of a flavoring agent represented by the formula:

$$CH_3(CH_2)_nCH(CH_3)OCOR$$

wherein n is 2 or 4 and R is a lower alkyl group having from 1 to 5 carbon atoms.

The present invention extends to methods for making the improved confections. The flavoring agents may be incorporated into an otherwise conventional hard or soft confection composition using standard techniques and equipment known to those skilled in the art. The apparatus useful in accordance with the present invention comprises mixing and heating apparatus well known in the confectionery manufacturing arts, and therefore the selection of the specific apparatus will be apparent to the artisan.

In such a method, a composition is made by admixing the inventive flavoring agent into the confectionery composition along with the other ingredients of the final desired composition. Other ingredients will usually be incorporated into the composition as dictated by the nature of the desired composition as well known by those having ordinary skill in the art. The ultimate confectionery compositions are readily prepared using methods generally known in the food technology and pharmaceutical arts. Thereafter the confectionery mixture may be formed into desirable confectionery shapes.

The flavoring agents may be formulated with conventional ingredients which offer a variety of textures to suit particular applications. Such ingredients may be in the form of hard and soft confections, tablets, toffee, nougat, chewy candy, chewing gum and so forth, center filled candies, both sugar and sugarless. The acceptable ingredients may be selected from a wide range of materials. Without being limited thereto, such materials include diluents, binders and adhesives, lubricants, disintegrants, bulking agents, humectants and buffers and adsorbents. The preparation of such confections and chewing gum products is well known.

The flavoring agents may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as butylated hydroxyanisole (BHA), butylated hydroxytoluene (BHT), benzoic acid, ascorbic acid, methyl paraben, propyl paraben, tocopherols, and the like, and mixtures thereof. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.01% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These colorants are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10%, and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the flavoring agent with the thickener-water admixture to form a uniform thickener-flavoring agent;

(D) combine the sweetener solution with the thickener-flavoring agent and mix until uniform; and (E) admix the optional adjunct materials such as coloring agents, flavoring agents, decolorants, solubilizers, antifoaming agents, buffers and additional water with the mixture of step (D) to form the suspension.

The flavoring agents of this invention may also be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The composition of the instant invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, *Pharmaceutical Dosage Forms: Tablets* Volume 1, Marcel Dekker, Inc., New York, N.Y. (1989) at pages 367 to 418, which disclosure is incorporated herein by reference.

In accordance with this invention, organoleptically effective amounts of the flavoring agents of the present invention may be admixed into the hard and soft confectionery products. These amounts are readily determined by those skilled in the art without the need for undue experimentation. In a preferred embodiment, the flavoring agent will comprise the flavoring agent in an amount from about 0.25% to about 2% and an ingestible vehicle, that is a pharmaceutically acceptable carrier, in a quantity sufficient to bring the total amount of composition to 100%, by weight the ingestible composition. In a more preferred embodiment, the composition will comprise the flavoring agent in an amount from about 0.05% to about 1% and an ingestible vehicle in a quantity sufficient to bring the total amount of composition to 100%, by weight the ingestible composition.

In another form of the invention, the flavoring agent is incorporated into an ingestible topical vehicle which may be in the form of a mouthwash, rinse, ingestible spray, suspension, dental gel, and the like. Typical non-toxic ingestible vehicles known in the pharmaceutical arts may be used in the present invention. The preferred ingestible vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the ingestible vehicle is generally from about 4 to about 7, and preferably from about 5 to about 6.5. An ingestible topical vehicle having a pH value below about 4 is generally irritating to the ingestible cavity and an ingestible vehicle having a pH value greater than about 7 generally results in an unpleasant mouth feel.

The ingestible topical flavoring agents may also contain conventional additives normally employed in those products. Conventional additives include a fluorine providing compound, a sweetening agent, a flavoring agent, a coloring agent, a humectant, a buffer, and an emulsifier, providing the additives do not interfere with the flavoring properties of the composition.

The coloring agents and humectants, and the amounts of these additives to be employed, set out above, may be used in the ingestible topical composition.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and di-fluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the present ingestible topical composition is dependent upon the type of fluorine providing compound employed, the solubility of the fluorine compound, and the nature of the final ingestible composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the ingestible topical composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof. Without being limited to particular sweetening agents, representative categories and examples include:

(a) water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1, 2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalacto-sucrose derivatives include but are not limited to: 1-chloro-1'-deoxysucrose; 4-chloro-4-deoxy-alpha-D-galacto-pyranosyl-alpha-D-fructofuranoside, or 4-chloro-4-deoxygalactosucrose; 4-chloro-4-deoxy-alpha-D-galacto-pyranosyl-1-chloro-1-deoxy-beta-D-fructo-furanoside, or 4,1'-dichloro-4,1'-dideoxygalactosucrose; 1',6'-dichloro-1',6'-dideoxysucrose; 4-chloro-4-deoxy-alpha-D-galacto-pyranosyl-1,6-dichloro-1,6-dideoxy-beta-D-fructo-furanoside, or 4,1',6'-trichloro-4,1',6'-trideoxygalacto-sucrose; 4,6-dichloro-4,6-dideoxy-alpha-D-galacto-pyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galacto-pyranosyl-1,6-dichloro-1,6-di-deoxy-beta-D-fructofuranoside, or 4,6,1',6'-tetrachloro-4,6,1',6'-tetradeoxygalacto-sucrose; and 4,6,1',6'-tetrachloro-4,6,1',6'-tetradeoxy-sucrose; and (e) protein based sweeteners such as thaumaoccous danielli (Thaumatin I and II).

In general, an effective amount of sweetening agent is utilized to provide the level of sweetness desired in the particular ingestible topical composition, and this amount will vary with the sweetener selected and the final ingestible product desired. The amount of sweetener normally present is in the range from about 0.0025% to about 90%, by weight of the ingestible topical composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the ingestible topical composition is normally a matter of preference subject to such factors as the type of final ingestible composition, the individual flavor employed, and the strength of flavor desired. Thus, the amount of flavoring may be varied in order to obtain the result desired in the final product and such variations are within the capabilities of those skilled in the art without the need for undue experimentation. The flavoring agents, when used, are generally utilized in amounts that may, for example, range in amounts from about 0.05% to about 6%, by weight of the ingestible topical composition.

Suitable buffer solutions useful in the non-ingestible topical flavoring agents include citric acid-sodium citrate solution, phosphoric acid-sodium phosphate solution, and acetic acid-sodium acetate solution in amounts up to about 1%, and preferably from about 0.05% to about 0.5% by weight of the ingestible topical composition.

In accordance with this invention, organoleptically effective amounts of the flavoring agents of the present invention may be admixed with an ingestible topical vehicle to form a topical composition. These amounts are readily determined by those skilled in the art without the need for undue experimentation. In a preferred embodiment, the ingestible topical flavoring agents will comprise the flavoring agent in an amount from about 0.025% to about 2% and an ingestible topical vehicle in a quantity sufficient to bring the total amount of composition to 100%, by weight of the ingestible topical composition. In a more preferred embodiment, the ingestible topical flavoring agents will comprise the flavoring agent in an amount from about 0.05% to about 1% and an ingestible topical vehicle in a quantity sufficient to bring the total amount of composition to 100%, by weight of the ingestible topical composition.

The present invention extends to methods for preparing the ingestible topical flavoring agents. In such a method, the ingestible topical composition is prepared by admixing an organoleptically effective amount of the flavoring agent of the present invention and an ingestible topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In a preferred embodiment, an ingestible topical composition is made by first dissolving coloring agents, sweetening agents, and similar additives in water. The flavoring agent is then admixed with the aqueous solution. Then sufficient water or ethanol, or mixtures of water and ethanol, are added to the solution with mixing until the final solution volume is reached. In a more preferred embodiment, the flavoring agent is added to the solution as the final ingredient. The final ingestible topical flavoring agents are readily prepared using methods generally known in the pharmaceutical arts.

The ingestible composition may also be in the form of dental gel. As used herein, the term "gel" means a solid or semisolid colloid which contains considerable quantities of water. The colloid particles in a gel are linked together in a coherent meshwork which immobilizes the water contained inside the meshwork.

The dental gel compositions of the present invention may contain the conventional additives set out above for ingestible topical flavoring agents such as mouthwashes, rinses, ingestible sprays, and suspensions and, in addition, may contain additional additives such as a polishing agent, a desensitizing agent, and the like, providing the additional additives do not interfere with the properties of the composition.

In a dental gel composition, the ingestible vehicle generally comprises water, typically in an amount from about 10% to about 90%, by weight of the dental gel composition. Polyethylene glycol, propylene glycol, glycerin, and mixtures thereof may also be present in the vehicle as humectants or binders in amounts from about 18% to about 30%, by weight of the dental gel composition. Particularly preferred ingestible vehicles comprise mixtures of water with polyethylene glycol or water with glycerin and polypropylene glycol.

The dental gels of the present invention include a gelling agent (thickening agent) such as a natural or synthetic gum or gelatin. Gelling agents such as hydroxyethyl cellulose, methyl cellulose, glycerin, carboxypolymethylene, and gelatin and the like, and mixtures thereof may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 1%, by weight, and sodium citrate may be used in an amount from about 0.3% to about 9%, and preferably from about 0.6% to about 3%, by weight of the dental gel composition.

In accordance with this invention, organoleptically effective amounts of the flavoring agents of the present invention may be admixed into the dental gel compositions. These amounts are readily determined by those skilled in the art without the need for undue experimentation. In a preferred embodiment, the dental gel compositions will comprise the flavoring agent in an amount from about 0.025% to about 2% and an ingestible topical vehicle in a quantity sufficient to bring the total amount of composition to 100%, by weight of the dental gel composition. In a more preferred embodiment, the dental gel compositions will comprise the flavoring agent in an amount from about 0.05% to about 1% and an ingestible topical vehicle in a quantity sufficient to bring the total amount of composition to 100%, by weight of the dental gel composition.

The present invention extends to methods for preparing the stabilized dental gel compositions. In such a method, the dental gel composition is prepared by admixing an organoleptically effective amount of the flavoring agent of the present invention and an ingestible topical vehicle. The final compositions are readily prepared using methods generally known by those skilled in the dental and pharmaceutical arts. The apparatus useful in accordance with the present invention comprises mixing apparatus well known in the pharmaceutical arts, and therefore the selection of the specific apparatus will be apparent to the artisan.

In a preferred embodiment, an dental gel composition is made by first dispersing a gelling agent in a humectant or water, or a mixture of both, then admixing to the dispersion an aqueous solution of the water-soluble additives such as the fluorine providing compound, sweeteners and the like, then adding the polishing agent, and lastly admixing the flavoring agent and the flavoring agent. The final gel mixture is then tubed or otherwise packaged. The liquids and solids in a gel product are proportioned to form a creamy or gelled mass which is extrudable from a pressurized container or from a collapsible tube. The final flavoring agents are readily prepared using methods generally known in the pharmaceutical arts.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLE 1

This example illustrates the preparation of 1-methylbutyl acetate, $CH_3(CH_2)_2CH(CH_3)OCOCH_3$, (pentyl-2-yl acetate).

2-Pentanol (176 g, 2.0 mol, Aldrich) and sodium acetate (18 g, 10 Aldrich) were heated to 90° C. and then acetic anhydride (240 ml, BDH GPR) was added over a 1 hour period at 100–110° C. The mixture was heated to reflux for 4 hours. The reaction mixture was then cooled, washed with water, washed with aqueous sodium bicarbonate to neutrality, dried over sodium sulfate, and then concentrated. Fractional distillation of the crude residue under vacuum provided 1-methylbutyl acetate (80–81°/140–145 mm Hg, 77% yield), the structure of which was confirmed by mass spectroscopy, nuclear magnetic resonance spectroscopy, and infra red spectroscopy (not shown).

EXAMPLE 2

This example illustrates the preparation of 1-methylbutyl butyrate, $CH_3(CH_2)_2CH(CH_3)OCO(CH_2)_2CH_3$, (pentyl-2-yl butyrate).

Butyric anhydride (400 ml, Aldrich) was added to 2-pentanol (176 g, 2.0 mol, Aldrich) over a 1.5 hour period at 100–120° C. The mixture was heated to 160° for 4 hours. The reaction mixture was then cooled, washed with hot water, washed with aqueous sodium carbonate to remove butyric anhydride, dried over sodium sulfate, and then concentrated. Fractional distillation of the crude residue under vacuum provided 1-methylbutyl butyrate (107–110°/115–120 mm Hg, 57% yield), the structure of which was confirmed by mass spectroscopy, nuclear magnetic resonance spectroscopy, and infra red spectroscopy (not shown).

EXAMPLE 3

This example illustrates the preparation of 1-methylhexyl acetate, $CH_3(CH_2)_4CH(CH_3)OCOCH_3$, (heptyl-2-yl acetate).

2-Heptanol (162 g, 1.4 mol, Aldrich) and sodium acetate (16 g, Aldrich) were heated to 100° C. and then acetic anhydride (190 ml, BDH GPR) was added over a 1 hour period at 100–130° C. The mixture was heated to reflux for 3 hours. The reaction mixture was then cooled, washed with water, washed with aqueous sodium bicarbonate to neutrality, dried over sodium sulfate, and then concentrated. Fractional distillation of the crude residue under vacuum provided 1-methylhexyl acetate (107–108°/95–100 mm Hg, 67% yield), the structure of which was confirmed by mass spectroscopy, nuclear magnetic resonance spectroscopy, and infra red spectroscopy (not shown).

EXAMPLE 4

This example illustrates the preparation of 1-methylhexyl butyrate, $CH_3(CH_2)_4CH(CH_3)OCO(CH_2)_2CH_3$, (heptyl-2-yl butyrate).

Butyric anhydride (260 ml, Aldrich) was added to 2-heptanol (162 g, 1.4 mol, Aldrich) over a 1.5 hour period at 100–140° C. The mixture was heated to 160° for 4 hours. The reaction mixture was then cooled, washed with hot water, washed with aqueous sodium carbonate to remove butyric anhydride, dried over sodium sulfate, and then concentrated. Fractional distillation of the crude residue under vacuum provided 1-methylhexyl butyrate (85–110°/78–80 mm Hg, 85% yield), the structure of which was confirmed by mass spectroscopy, nuclear magnetic resonance spectroscopy, and infra red spectroscopy (not shown).

EXAMPLE 5

This example summarizes the flavor evaluation results obtained comparing the novel flavoring agents of the present invention versus control compounds.

FLAVOR INGREDIENT EVALUATION RESULTS

Eight (8) flavorists evaluated four flavor compounds of the present invention together with 2 common chemically related esters. For all compounds, odor assessments were made at 1000 ppm and all were tasted at 10 ppm in 5% sucrose solution. A summary of odor and flavor descriptors together with their ideas of suggested usage and an interest rating score are given below:

| Name | Odor Descriptors | Taste Descriptors | Suggested Usage | Interest Rating |
|---|---|---|---|---|
| iso-Amy Acetate | fruity, ethereal banana, pear | fruity, sweet, banana weak | Fruit, Pear Banana | 8 |
| Pen-2-yl Acetate | fruity, ripe banana herbal, green ethereal | fruity, ripe banana creamy, green | Banana, Pear Apple, Mango, Pineapple | 8 |
| Pent-2-yl Butyrate | fruity, berry powdery, perfumed, dry | sweet, fruity, banana blueberry, powdery | Banana Strawberry Blueberry, Cherry | 7 |
| Heptyl Acetate | green, soapy, waxy herbal, fruity | soapy, waxy, green fruity | Melon, Pear Coconut | 6 |
| Hept-2-yl Acetate | fruity, melon, green fatty | banana flesh, melon, pear, fruity, green | Banana, Pear Melon | 6 |
| Hept-2-yl Butyrate | fatty, pear, green fruity, banana skin pineapple | fleshy, banana, fruity pear, skin, creamy green | Banana, Pear Strawberry, Pineapple | 7 |

The interest rating score relates to a 9 point hedonic scale where

| | |
|---|---|
| 9 | like extremely |
| 8 | like very much |
| 7 | like moderately |
| 6 | like slightly |
| 5 | neither like nor dislike |
| 4 | dislike slightly |
| 3 | dislike moderately |
| 2 | dislike very much |
| 1 | dislike extremely |

In summary, the panel results show that the odor and taste characteristics of the flavor chemicals of the present invention have a beneficial effect on the overall profile of Banana flavor.

The invention being thus described, it will be obvious that the same may be varied in many ways. Such variations are not to be regarded as a departure from the spirit and scope of the invention and all such modifications are intended to be included within the scope of the following claims.

I claim:

1. A method for flavoring an ingestible composition which comprises admixing an ingestible vehicle with an organoleptically effective amount of a flavoring agent, wherein the flavoring agent is unaccompanied by substances of natural origin present in banana and is represented by the formula:

$$CH_3(CH_2)_nCH(CH_3)OCOR$$

wherein n is 2 or 4 and R is a lower alkyl group having from 1 to 5 carbon atoms.

2. The method according to claim 1, wherein n is 2.

3. The method according to claim 1, wherein n is 4.

4. The method according to claim 1, wherein R is methyl.

5. The method according to claim 1, wherein R is propyl.

6. The method according to claim 1, wherein the flavoring agent is 1-methylbutyl acetate.

7. The method according to claim 1, wherein the flavoring agent is 1-methylbutyl butyrate.

8. The method according to claim 1, wherein the flavoring agent is 1-methylhexyl acetate.

9. The method according to claim 1, wherein the flavoring agent is 1-methylhexyl butyrate.

10. The method according to claim 1, wherein the flavoring agent is a mixture of 1-methylbutyl acetate, present in an amount of from about 2% to about 10%, 1-methylbutyl butyrate, present in an amount of from about 2% to about 10%, and 1-methylhexyl butyrate, present in an amount of from about 0.1% to about 5%, by weight.

11. The method according to claim 1, wherein the ingestible composition is a confectionery composition.

12. The method according to claim 1, wherein the ingestible composition is a chewing gum composition.

* * * * *